(12) United States Patent
Heath

(10) Patent No.: US 8,097,792 B2
(45) Date of Patent: Jan. 17, 2012

(54) SWEET GRAPE TOMATO LINE CHD 15-2114

(75) Inventor: Douglas William Heath, Rocklin, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 0 days.

(21) Appl. No.: 12/905,987

(22) Filed: Oct. 15, 2010

(65) Prior Publication Data

US 2011/0088108 A1    Apr. 14, 2011

Related U.S. Application Data

(62) Division of application No. 12/139,311, filed on Jun. 13, 2008, now Pat. No. 7,816,583.

(60) Provisional application No. 60/966,546, filed on Jun. 13, 2007.

(51) Int. Cl.
 A01H 5/08     (2006.01)
 C07H 21/04   (2006.01)
 C07K 14/415  (2006.01)
 C12N 15/00   (2006.01)
 A01H 1/00     (2006.01)

(52) U.S. Cl. ............ 800/317.4; 435/468; 435/411; 530/370; 536/23.1; 800/278; Plt./261

(58) Field of Classification Search ............ 435/411; 530/370; 536/23.6; 800/317.4; Plt./261; 426/106, 615
See application file for complete search history.

(56) References Cited

U.S. PATENT DOCUMENTS

| 6,180,854 B1 | 1/2001 | Morrison et al. |
| 6,340,785 B1 * | 1/2002 | Thome et al. ............ 800/317.4 |
| 6,806,399 B1 | 10/2004 | Korol et al. |
| 2009/0064367 A1 | 3/2009 | Heath |

OTHER PUBLICATIONS

Application for European Union Community Plant Variety Right for Tomato Variety CHI 15-2113, filed May 16, 2007.
Application for Plant Breeders' Rights for Tomato Variety BS 01543756, filed Jan. 26, 2007, The Netherlands.
Application for Plant Breeders' Rights for Tomato Variety CHI 15-2113, filed Feb. 14, 2007, The Netherlands.

* cited by examiner

*Primary Examiner* — Phuong Bui
(74) *Attorney, Agent, or Firm* — SNR Denton US LLP; Alissa Eagle, Esq.

(57) ABSTRACT

The invention provides seed and plants of tomato line CHI 15-2113, tomato line CHD 15-2114 and hybrid tomato variety BX 0154 3756. The invention thus relates to the plants, seeds and tissue cultures of tomato line CHI 15-2113, tomato line CHD 15-2114 and hybrid tomato variety BX 0154 3756, and to methods for producing a tomato plant produced by crossing a plant of tomato line CHI 15-2113, tomato line CHD 15-2114 or hybrid tomato variety BX 0154 3756 with itself or with another tomato plant, such as a plant of another line or variety. The invention further relates to seeds and plants produced by such crossing. The invention further relates to parts of a plant of tomato line CHI 15-2113, tomato line CHD 15-2114 or hybrid tomato variety BX 0154 3756, including the fruit and gametes of such plants.

26 Claims, No Drawings

SWEET GRAPE TOMATO LINE CHD 15-2114

This application is a divisional of U.S. application Ser. No. 12/139,311, filed Jun. 13, 2008 now U.S. Pat. No. 7,816,583, which application claims the priority of U.S. Provisional Appl. Ser. No. 60/966,546, filed Jun. 13, 2007, the entire disclosures of which are incorporated herein by reference.

BACKGROUND OF THE INVENTION

1. Field of the Invention

The present invention relates to the field of plant breeding and, more specifically, to the development of tomato line CHI 15-2113, tomato line CHD 15-2114 and tomato variety BX 0154 3756.

2. Description of Related Art

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for a uniform type over many generations become homozygous at almost all gene loci and produce a uniform population of true breeding progeny of homozygous plants. A cross between two such homozygous plants of different varieties produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants, and the evaluation of the crossed progeny. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop species that has been subject to such breeding programs and is of particular value is the tomato. The common tomato, *Solanum lycopersicum* (formerly *Lycopersicon esculentum* Mill.) is widely cultivated domestically and internationally. Of the approximately 500,000 acres of tomatoes grown annually in the United States, roughly 40% are grown for fresh market consumption, with the balance grown for processing.

Most cultivated tomatoes are diploid, self-fertile and mostly self-pollinating, with hermaphroditic flowers. Tomatoes having different ploidy levels are not uncommon and were already known in the 1920's and 30's (Linstrom, 1940). Prior to the mid-1970's, most commercial cultivars were pure breeding lines. Since then, better performing hybrid cultivars have been replacing the pure breeding lines. Today, most commercial varieties are hybrids. Due to its wide dissemination and high value, the tomato species has been intensively bred, providing a wide variety of lines with different traits. Tomato fruits from different cultivars show tremendous variation in weight and shape. Common groupings in the marketplace include the cherry, plum, pear, standard (or round), and beefsteak types.

While breeding efforts to date have provided a number of useful tomato lines and varieties with beneficial traits, there remains a great need in the art for new lines and varieties with further improved traits. Such plants would benefit farmers and consumers alike by improving crop yield and/or fruit quality.

SUMMARY OF THE INVENTION

In one aspect, the invention provides tomato plants comprising at least a first set of the chromosomes of tomato line CHI 15-2113 or tomato line CHD 15-2114. In another aspect, the present invention provides a tomato plant of said lines or progeny thereof, such as a hybrid tomato plant of the variety BX 0154 3756 or progeny thereof. Also provided are tomato plants having all the physiological and morphological characteristics of tomato line CHI 15-2113, tomato line CHD 15-2114 or hybrid tomato variety BX 0154 3756. Parts of the tomato plants of the present invention are also provided, for example, including pollen, an ovule, a fruit, a scion, a rootstock and a cell of the plant.

The invention also concerns seed of tomato line CHI 15-2113, tomato line CHD 15-2114 and tomato variety BX 0154 3756. The tomato seed of the invention may be provided as an essentially homogeneous population of tomato seed. Essentially homogeneous populations of seed are generally free from substantial numbers of other seed. Therefore, seed of line CHI 15-2113, line CHD 15-2114 and tomato variety BX 0154 3756 may be defined as forming at least about 97% of the total seed, including at least about 98%, 99%, or more of the seed. In certain embodiments, the population of tomato seed may be particularly defined as being essentially free from hybrid seed. The seed population may be separately grown to provide an essentially homogeneous population of tomato plants designated tomato line CHI 15-2113, tomato line CHD 15-2114 and tomato variety BX 0154 3756.

In another aspect of the invention, tissue cultures of regenerable cells of plants of tomato line CHI 15-2113, tomato line CHD 15-2114 and hybrid tomato variety BX 0154 3756 are provided. Such a tissue culture will preferably be capable of regenerating plants capable of expressing all of the physiological and morphological characteristics of a plant of tomato line CHI 15-2113, tomato line CHD 15-2114 or hybrid tomato variety BX 0154 3756, and of regenerating plants having substantially the same genotype as either or these. Examples of some of the physiological and morphological characteristics of this line and variety include those traits set forth in the respective tables herein. The regenerable cells in such tissue cultures may be derived, for example, from embryos, meristems, cotyledons, pollen, leaves, anthers, roots, root tips, pistil, flower, seed and stalks. Still further, the present invention provides tomato plants regenerated from a tissue culture of the invention, the plants having all the physiological and morphological characteristics of a plant of tomato line CHI 15-2113, tomato line CHD 15-2114 or hybrid tomato variety BX 0154 3756.

The invention also concerns methods of vegetatively propagating a plant of tomato line CHI 15-2113, tomato line CHD 15-2114 or hybrid tomato variety BX 0154 3756. In certain embodiments, the method comprises the steps of: (a) collecting tissue capable of being propagated from a plant of tomato line CHI 15-2113, tomato line CHD 15-2114 or hybrid tomato variety BX 0154 3756; (b) cultivating said tissue to obtain proliferated shoots; and (c) rooting said proliferated shoots to obtain rooted plantlets. In some of these embodiments, the method further comprises growing plants from said rooted plantlets.

In further aspects, the invention provides genetic complement of tomato line CHI 15-2113 or tomato line CHD 15-2114. It yet further aspects, it also provides hybrid genetic complements, as represented by tomato plant cells, tissues, plants, and seeds, formed by the combination of a haploid genetic complement of a tomato plant of tomato line CHI 15-2113 or tomato line CHD 15-2114 with a haploid genetic complement of a second tomato plant, preferably, another, distinct tomato plant. For example, the genetic complement of hybrid tomato variety BX 0154 3756 is provided. In other embodiments, the present invention provides a tomato plant regenerated from a tissue culture that comprises a hybrid genetic complement of this invention.

The phrase "genetic complement" is used to refer to the aggregate of nucleotide sequences, the expression of which defines the phenotype of, in the present case, a tomato plant of, or a cell or tissue of that plant. A genetic complement thus represents the genetic makeup of a cell, tissue or plant, and a hybrid genetic complement represents the genetic make up of a hybrid cell, tissue or plant. The invention thus provides tomato plant cells that have a genetic complement in accordance with the tomato plant cells disclosed herein, and plants, seeds and plants containing such cells.

Plant genetic complements may be assessed by genetic marker profiles, and by the expression of phenotypic traits that are characteristic of the expression of the genetic complement, e.g., gene expression profiles, gene product expression profiles and isozyme typing profiles. It is understood that line CHI 15-2113, line CHD 15-2114 or a first generation progeny, such as hybrid tomato variety BX 0154 3756, could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In another aspect, the invention provides a method of determining the genotypes of tomato plants, such as those of tomato line CHI 15-2113, tomato line CHD 15-2114 or hybrid tomato variety BX 0154 3756, comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In yet another aspect, the invention provides a plant of a hybrid tomato variety that exhibits a trait comprising a capacity to produce mature fruit having a sugar content from about 9.0 degrees Brix to about 10.0 degrees Brix and a weight from about 6.0 g to about 8.0 g. In certain embodiments, the trait may be defined as controlled by genetic means for the expression of the trait found in tomato variety BX 0154 3756.

In still yet another aspect, the invention provides a plant of a grape tomato variety that exhibits a combination of traits comprising resistance to tomato mosaic virus and a capacity to produce mature fruit having a sugar content from about 9.0 degrees Brix to about 10.0 degrees Brix. In some embodiments, the plant is resistant to all races of tomato mosaic virus; in other embodiments the plant is resistant to races 0, 1, and 2 of tomato mosaic virus. In certain embodiments, the combination of traits may be defined as controlled by genetic means for the expression of the combination of traits found in tomato variety BX 0154 3756.

In a further aspect of the invention, the sugar content of the mature fruit falls within a range, for example, having a lower value of about 8.5, 8.6, 8.7, 8.8, 8.9, 9.0, 9.1, 9.2, 9.3, 9.4, or 9.5 degrees Brix, and an upper value of about 10.0, 10.1, 10.2, 10.3, 10.4, 10.5, 10.6, 10.7, 10.8, 10.9 or 11.0 degrees Brix, including all ranges derivable therefrom.

In another aspect of the invention, the weight of the mature fruit falls within a range, for example, having a lower value of about 5.0, 5.1, 5.2, 5.3, 5.4, 5.5, 5.6, 5.7, 5.8, 5.9, 6.0, 6.1, 6.2, 6.3, 6.4, or 6.5 grams, and an upper value of about 7.5, 7.6, 7.7, 7.8, 7.9, 8.0, 8.1, 8.2, 8.3, 8.4, 8.5, 8.6, 8.7, 8.8, 8.9 or 9.0 grams, including all ranges derivable therefrom.

In certain embodiments, the present invention provides a method of producing tomatoes comprising: (a) obtaining a plant of tomato line CHI 15-2113, tomato line CHD 15-2114 or hybrid tomato variety BX 0154 3756, wherein the plant has been cultivated to maturity, and (b) collecting tomatoes from the plant.

In yet another aspect of the invention, processes are provided for producing tomato seeds, plants and fruit, which processes generally comprise crossing a first parent tomato plant with a second parent tomato plant, wherein at least one of the first or second parent tomato plants is a plant of line CHI 15-2113, line CHD 15-2114 or variety BX 0154 3756. These processes may be further exemplified as processes for preparing hybrid tomato seed or plants, wherein a first tomato plant is crossed with a second tomato plant of a different, distinct line to provide a hybrid that has, as one of its parents, the tomato plant line CHI 15-2113 or line CHD 15-2114. In one embodiments of the invention, tomato lines CHI 15-2113 and CHD 15-2114 are crossed to produce hybrid seed of the variety designated BX 0154 3756. In any cross herein, either parent may be the male or female parent. In certain embodiments the female parent of the hybrid is a plant of line CHI 15-2113. In the above processes, crossing will result in the production of seed. The seed production occurs regardless of whether the seed is collected or not.

In one embodiment of the invention, the first step in "crossing" comprises planting seeds of a first and second parent tomato plant, often in proximity so that pollination will occur for example, mediated by insect vectors. Alternatively, pollen can be transferred manually.

A second step may comprise cultivating or growing the seeds of first and second parent tomato plants into plants that bear flowers. A third step may comprise preventing self-pollination of the plants, such as by emasculating the male portions of flowers, (i.e., treating or manipulating the flowers to produce an emasculated parent tomato plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent tomato plants. Yet another step comprises harvesting the seeds from at least one of the parent tomato plants. The harvested seed can be grown to produce a tomato plant or hybrid tomato plant.

The present invention also provides the tomato seeds and plants produced by a process that comprises crossing a first parent tomato plant with a second parent tomato plant, wherein at least one of the first or second parent tomato plants is a plant of line CHI 15-2113, line CHD 15-2114 or variety BX 0154 3756. In one embodiment of the invention, tomato seed and plants produced by the process are first generation ($F_1$) hybrid tomato seed and plants produced by crossing a plant in accordance with the invention with another, distinct plant. In one such embodiment, the first generation ($F_1$) hybrid tomato seed and plants produced are of the hybrid tomato variety designated BX 0154 3756. The present invention further contemplates plant parts of such an $F_1$ hybrid tomato plant, and methods of use thereof. Therefore, certain exemplary embodiments of the invention provide an $F_1$ hybrid tomato plant and seed thereof.

In another aspect, the present invention provides a method of producing a plant or a seed derived from tomato line CHI 15-2113, tomato line CHD 15-2114 or hybrid tomato variety BX 0154 3756, the method comprising the steps of: (a) preparing a progeny plant derived from tomato line CHI 15-2113, tomato line CHD 15-2114 or hybrid tomato variety BX 0154 3756, wherein said preparing comprises crossing a plant of tomato line CHI 15-2113, tomato line CHD 15-2114 or hybrid tomato variety BX 0154 3756 with a second plant; and (b) selfing the progeny plant or crossing it to the second plant or to a third plant to produce a seed of a progeny plant of a subsequent generation. In certain embodiments, the plant of tomato line CHI 15-2113, tomato line CHD 15-2114 or hybrid tomato variety BX 0154 3756 is the female parent. In other embodiments the plant of tomato line CHI 15-2113, tomato line CHD 15-2114 or hybrid tomato variety BX 0154 3756 is the male parent.

The method may additionally comprise: (c) growing a progeny plant of a subsequent generation from said seed of a progeny plant of a subsequent generation and selfing the progeny plant of a subsequent generation or crossing it to the second, the third, or a further plant; and repeating the steps for an additional 3-10 generations to produce a further plant derived from tomato line CHI 15-2113, tomato line CHD 15-2114 or hybrid tomato variety BX 0154 37560. The further plant derived from tomato line CHI 15-2113, tomato line CHD 15-2114 or hybrid tomato variety BX 0154 3756 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from tomato line CHI 15-2113, tomato line CHD 15-2114 or hybrid tomato variety BX 0154 3756 is obtained which possesses some of the desirable traits of the variety as well as potentially other selected traits.

In a further embodiment, the invention provides for the plants and seeds produced by the above process.

In additional embodiments, the method provided by the invention further comprises doubling the chromosome number of tomato line CHI 15-2113, tomato line CHD 15-2114 or hybrid tomato variety BX 0154 3756 to produce a tetraploid tomato plant.

In another aspect of the invention, a plant of tomato line CHI 15-2113, tomato line CHD 15-2114 or hybrid tomato variety BX 0154 3756 comprising an added heritable trait is provided. The heritable trait may comprise a genetic locus that is, for example, a dominant or recessive allele. In one embodiment of the invention, a plant of tomato line CHI 15-2113 or tomato line CHD 15-2114 is defined as comprising a single locus conversion. For example, one or more heritable traits may be introgressed at any particular locus using a different allele that confers the new trait or traits of interest. In specific embodiments of the invention, the single locus conversion confers one or more traits such as, for example, herbicide tolerance, insect resistance, disease resistance and modulation of plant metabolism and metabolite profiles. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

For example, in certain embodiments, the invention provides methods of introducing a desired trait into a plant of the invention comprising: (a) crossing a plant of tomato line CHI 15-2113, tomato line CHD 15-2114 or hybrid tomato variety BX 0154 3756 with a second tomato plant that comprises a desired trait to produce F1 progeny, (b) selecting an F1 progeny that comprises the desired trait, (c) crossing the selected F1 progeny with a plant of tomato line CHI 15-2113, tomato line CHD 15-2114 or hybrid tomato variety BX 0154 3756 to produce backcross progeny, and (d) selecting backcross progeny comprising the desired trait and the physiological and morphological characteristic of tomato line CHI 15-2113, tomato line CHD 15-2114 or hybrid tomato variety BX 0154 3756. The invention also provides tomato plants produced by these methods.

Any embodiment discussed herein with respect to one aspect of the invention applies to other aspects of the invention as well, unless specifically noted.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, plant parts, seeds and derivatives of hybrid tomato variety BX 0154 3756, as well as parent plants capable of being crossed to produce this variety, designated tomato line CHI 15-2113 and tomato line CHD 15-2114. In general, all three can be characterized as orange grape tomatoes.

Hybrid tomato variety BX 0154 3756 exhibits a number of improved traits such as high sugar content, resistance to tomato mosaic virus (also referred to as tobacco mosaic virus, see e.g. Table 3, below), and fruit having an average weight at maturity of about 7.0 grams, a light green shoulder that does not persist when the fruit is mature, and jointed fruit attachment. The variety also exhibits resistance to a number of diseases, including *Verticillium* wilt race 1, *Fusarium* Wilt race 1, all races of Tomato Mosaic Virus resistance, including races 0, 1, and 2, *Alternaria* Stem Canker, and Bacterial Speck race 0. Thus this variety is well suited to commercial production, including green house production. As with its parent lines, the variety may exhibit a minor degree of parthenocarpy. This variety shows genetic uniformity and stability and horticultural uniformity and stability within the limits of environmental influence for the traits described hereinafter. The parents of BX 0154 3756 are particularly useful for the production of hybrid varieties based on the beneficial traits conferred in hybrid combination.

The development of the lines and varieties of this invention can be summarized as follows.

A. Origin and Breeding History

The parental inbred lines of hybrid orange grape tomato BX 0154 3756 were derived by crossing determinate red grape tomato CHD 15-2059 with orange cherry 'OC-1'. Line OC-1 was characterized by high levels of sugar and an orange cherry color resulting from the presence of the tangerine (tan) gene, a monogenic recessive.

This hybrid was selfed and a large F2 population was grown in a greenhouse in Woodland, Calif. Out of nine total F2 selections, two fixed orange (tangerine gene) selections were flagged for various attributes. One was line CHI 15-2113. This line was fixed indeterminate, but Tomato Mosaic Virus (ToMV) susceptible. The other line, CHD 15-2114, was fixed determinate and ToMV resistant. These two lines continued to be selfed and selected, fixing resistance to *Fusarium* wilt (*Fusarium oxysporum* f. sp. *lycopersici*) race 1, *Alternaria* Stem Canker (*Alternaria alternata* f. sp. *lycopersici*), and Bacterial Speck (*Pseudomonas syringae* pv. *tomato*) race 0 in each line. At least one of the parents was fixed for resistance to *Verticillium* wilt (*Verticillium dahliae*) race 1. After these lines were fixed for all disease resistances cited above and for horticultural characteristics related to productivity, quality and goodness of fit for market needs, they were progeny increased. During the progeny increases, each line remained fixed and stable. Each line also provides sufficient seed yield.

By crossing parent plant lines CHI 15-2113, as the female parent, and CHD 15-2114, as the male parent, uniform F1 hybrid progeny were obtained, designated BX 0154 3756. The sugar content achieved in the mature fruit of the F1 progeny was higher than in the mature fruit of either parent, with laboratory testing indicating degrees Brix around 9, 10 or higher. This is about 2 degree Brix higher than current grape tomatoes in the market. Combined with a fairly moderate level of acidity, BX 0154 3756 is markedly sweeter tasting than most other tomato varieties tested. Further, the orange cherry germplasm of this variety comprises resistance to all races of Tomato mosaic virus (ToMV), which extends the suitability of this variety to greenhouse production, as well as field production.

B. Physiological and Morphological Characteristics

Tomato cultivars may be grouped by maturity, i.e. the time required from planting the seed to the stage where fruit harvest can occur. Standard maturity classifications include 'early', 'midseason' or 'late-maturing'. Another classification for tomatoes is the developmental timing of fruit set. 'Determinant' plants grow foliage, then transition into a reproductive phase of flower setting, pollination and fruit development. Consequently, determinant cultivars have a large proportion of the fruit ripen within a short time frame. Growers that harvest only once in a season favor determinant type cultivars. In contrast, 'indeterminate' types grow foliage, then enter a long phase where flower and fruit development proceed along with new foliar growth. Growers that harvest the same plants multiple times favor indeterminate type cultivars. In response to more recent consumer demands for dietary diversity, tomato breeders have developed a wider range of colors. In addition to expanding the range of red colored fruits, there are cultivars that produce fruits that are creamy white, lime green, yellow, green, golden, orange and purple. Additionally, there are multi-colored varieties exemplified by mainly red fruited lines with green shoulders, and both striped- and variegated-colored fruit. Standard methods for determining tomato fruit color are described, for instance, in Gull et al. (1989) and Kader et al. (1978), both of which are incorporated by reference herein.

In accordance with one aspect of the present invention, there is provided a plant having the physiological and morphological characteristics of tomato line CHI 15-2113. A description of the physiological and morphological characteristics of tomato line CHI 15-2113 is presented in Table 1.

TABLE 1

Physiological and Morphological Characteristics of Line CHI 15-2113

| CHARACTERISTIC | Value for Line CHI 15-2113* |
|---|---|
| 1. Seedling | |
|    Anthocyanin in hypocotyl of 2-15 cm seedling | Present |
|    Habit of 3-4 week old seedling | Normal |
| 2. Mature Plant | 200 cm Height |
|    Growth | Indeterminate |
|    Form | Lax, open |
|    Size of canopy (compared to others) | Medium |
|    Habit | Sprawling (decumbent) |
| 3. Stem | |
|    Branching | Sparse ('Brehm's Solid Red', 'Fireball') |
|    Branching at cotyledonary or first leafy node | Absent |
|    No. of nodes below the first inflorescence | 4-6 |
|    No. of nodes between early ($1^{st}$-$2^{nd}$, $2^{nd}$-$3^{rd}$) inflorescences | 3-4 |
|    No. of nodes between later-developing inflorescences | 3-4 |
|    Pubescence on younger stems | Sparsely hairy (scattered long hairs) |
| 4. Leaf (mature leaf beneath the $3^{rd}$ inflorescence) | |
|    Type | Tomato |
|    Margins of major leaflets | Shallowly toothed or scalloped |
|    Marginal rolling or wiltiness | Slight |
|    Onset of leaflet rolling | Late season |
|    Surface of major leaflets | Smooth |
|    Pubescence | Normal |
| 5. Inflorescence (made observation on $3^{rd}$ inflorescence) | |

TABLE 1-continued

Physiological and Morphological Characteristics of Line CHI 15-2113

| CHARACTERISTIC | Value for Line CHI 15-2113* |
|---|---|
| Type | Simple |
| Number of flowers in inflorescence, average | 10 |
| Leafy or "running" inflorescences | Absent |
| 6. Flower | |
| Calyx | Normal, lobes awl-shaped |
| Calyx-lobes | Approx. equaling corolla |
| Corolla color | Yellow |
| Style pubescence | Sparse |
| Anthers | All fused into tube |
| Fasciation (1st flower of 2nd or 3rd inflorescence) | Absent |
| 7. Fruit (3rd fruit of 2nd or 3rd cluster) | |
| Abscission layer | Present (jointed) |
| Point of detachment of fruit at harvest | Generally at stem scar, but sometimes at calyx |
| Length of pedicel (from joint to calyx attachment) | 8 mm |
| Length of mature fruit (stem axis) | 26 mm |
| Diameter of fruit at widest point | 18 mm |
| Weight of mature fruit | 7 g |
| No. of locules | 2 |
| Fruit surface | Smooth |
| Fruit base color (mature-green stage) | Light green |
| Fruit pattern (mature green stage) | Uniform green |
| Shoulder color | Light green |
| Fruit color - full ripe | Orange |
| Flesh color - full ripe | Orange |
| Flesh color | Uniform |
| Locular gel color of table-ripe fruit | Yellow |
| Ripening | Uniform |
| Epidermis color | Yellow |
| Epidermis | Normal |
| Epidermis texture | Tender |
| Thickness of pericarp | Under 3 mm |
| 8. Disease and Pest Reaction | |
| Viral | |
| Tobacco mosaic, Race 0 | Susceptible |
| Tobacco mosaic, Race 1 | Susceptible |
| Tobacco mosaic, Race 2 | Susceptible |
| Tomato spotted wilt | Susceptible |
| Tomato yellows | Susceptible |
| Bacterial | |
| Bacterial canker (*Corynebacterium michiganense*) | Susceptible |
| Bacterial speck (*Pseudomonas tomato*) | Resistant |
| Bacterial spot (*Xanthomonas vesicatorium*) | Susceptible |
| Bacterial wilt (*Pseudomonas solanacearum*) | Susceptible |
| Fungal | |
| Brown root rot or corky root (*Pyrenochaeta lycopersici*) | Susceptible |
| *Fusarium* wilt, Race 1 | Resistant |
| *Fusarium* wilt, Race 2 | Susceptible |
| *Fusarium* wilt, Race 3 | Susceptible |
| Gray leaf spot (*Stemphylium* spp.) | Susceptible |
| 9. Chemistry and Composition of Full-Ripe Fruits | |
| pH | 4.69 |
| Titratable acidity, as % citric | 5.58 |
| Total solids (dry matter, seeds and skin removed) | 9.98 |
| Soluble solids, as °Brix | 8.57 |
| 10. Phenology | |
| Seeding to 50% flower (1 open flower on 50% of plants) | 45 days |
| Seed to once-over harvest | 78 days |
| Fruiting season | Medium |
| Relative maturity in areas tested | Early |
| 11. Adaptation | |
| Culture | Greenhouse |
| Principal use | Fresh market |
| Machine harvest | Not adapted |
| Regions to which adaptation has been demonstrated | California: Sacramento and Upper San Joaquin Valley |

*These are typical values. Values may vary due to environment. Other values that are substantially equivalent are within the scope of the invention.

Seed of tomato line CHI 15-2113 has been planted in different years. The plants grown from this seed have shown homozygosity and phenotypic stability to make it useful in commercial tomato or tomato seed production. No variant traits have been observed or are expected for this variety.

Also in accordance with one aspect of the present invention, there is provided a plant having the physiological and morphological characteristics of tomato line CHD 15-2114. A description of the physiological and morphological characteristics of tomato line CHD 15-2114 is presented in Table 2.

TABLE 2

Physiological and Morphological Characteristics of Line CHD 15-2114

| CHARACTERISTIC | Value for Line CHD 15-2114* |
|---|---|
| 1. Seedling | |
| Anthocyanin in hypocotyl of 2-15 cm seedling | Present |
| Habit of 3-4 week old seedling | Normal |
| 2. Mature Plant | 120 cm Height |
| Growth | Determinate |
| Form | Lax. open |
| Size of canopy (compared to others) | Medium |
| Habit | Sprawling (decumbent) |
| 3. Stem | |
| Branching | Sparse ('Brehm's Solid Red', 'Fireball') |
| Branching at cotyledonary or first leafy node | Absent |
| No. of nodes below the first inflorescence | 4-6 |
| No. of nodes between early (1st-2nd, 2nd-3rd) inflorescences | 3-4 |
| No. of nodes between later-developing inflorescences | 3-4 |
| Pubescence on younger stems | Sparsely hairy (scattered long hairs) |
| 4. Leaf (mature leaf beneath the 3rd inflorescence) | |
| Type | Tomato |
| Margins of major leaflets | Shallowly toothed or scalloped |
| Marginal rolling or wiltiness | Slight |
| Onset of leaflet rolling | Late season |
| Surface of major leaflets | Smooth |
| Pubescence | Normal |
| 5. Inflorescence (made observation on 3rd inflorescence) | |
| Type | Simple |
| Number of flowers in inflorescence, average | 10 |
| Leafy or "running" inflorescences | Absent |
| 6. Flower | |
| Calyx | Normal, lobes awl-shaped |
| Calyx-lobes | Approx. equaling corolla |
| Corolla color | Yellow |
| Style pubescence | Sparse |

TABLE 2-continued

Physiological and Morphological Characteristics of Line CHD 15-2114

| CHARACTERISTIC | Value for Line CHD 15-2114* |
|---|---|
| Anthers | All fused into tube |
| Fasciation (1$^{st}$ flower of 2$^{nd}$ or 3$^{rd}$ inflorescence) | Absent |
| 7. Fruit (3$^{rd}$ fruit of 2$^{nd}$ or 3$^{rd}$ cluster) | |
| Abscission layer | Present (jointed) |
| Point of detachment of fruit at harvest | Generally at stem scar, but sometimes at calyx |
| Length of pedicel (from joint to calyx attachment) | 8 mm |
| Length of mature fruit (stem axis) | 25 mm |
| Diameter of fruit at widest point | 20 mm |
| Weight of mature fruit | 7.5 g |
| No. of locules | 2 |
| Fruit surface | Smooth |
| Fruit base color (mature-green stage) | Medium green |
| Fruit pattern (mature green stage) | Green shoulder |
| Shoulder color | Dark green [at mature green] |
| Fruit color - full ripe | Orange |
| Flesh color - full ripe | Orange |
| Flesh color | Uniform |
| Locular gel color of table-ripe fruit | Yellow |
| Ripening | Uniform |
| Epidermis color | Yellow |
| Epidermis | Normal |
| Epidermis texture | Tender |
| Thickness of pericarp | Under 3 mm |
| 8. Disease and Pest Reaction | |
| Viral | |
| Tobacco mosaic, Race 0 | Resistant |
| Tobacco mosaic, Race 1 | Resistant |
| Tobacco mosaic, Race 2 | Resistant |
| Tomato spotted wilt | Susceptible |
| Tomato yellows | Susceptible |
| Bacterial | |
| Bacterial canker (*Corynebacterium michiganense*) | Susceptible |
| Bacterial speck (*Pseudomonas tomato*) | Resistant [race 0] |
| Bacterial spot (*Xanthomonas vesicatorium*) | Susceptible |
| Bacterial wilt (*Pseudomonas solanacearum*) | Susceptible |
| Fungal | |
| Brown root rot or corky root (*Pyrenochaeta lycopersici*) | Susceptible |
| *Fusarium* wilt, Race 1 | Resistant |
| *Fusarium* wilt, Race 2 | Susceptible |
| *Fusarium* wilt, Race 3 | Susceptible |
| Gray leaf spot (*Stemphylium* spp.) | Susceptible |
| 9. Chemistry and Composition of Full-Ripe Fruits | |
| pH | 4.88 |
| Titratable acidity, as % citric | 4.12 |
| Total solids (dry matter, seeds and skin removed) | 9.94 |
| Soluble solids, as °Brix | 9.19 |
| 10. Phenology | |
| Seeding to 50% flower (1 open flower on 50% of plants) | 45 days |
| Seed to once-over harvest | 76 days |
| Fruiting season | Early-Medium |
| Relative maturity in areas tested | Very Early |
| 11. Adaptation | |
| Culture | Greenhouse |
| Principal use | Fresh market |
| Machine harvest | Not adapted |
| Regions to which adaptation has been demonstrated | California: Sacramento and Upper San Joaquin Valley, Ontario, Canada, Sinaloa, Mexico |

*These are typical values. Values may vary due to environment. Other values that are substantially equivalent are within the scope of the invention.

Seed of tomato line CHD 15-2114 has been planted in different years. The plants grown from this seed have shown homozygosity and phenotypic stability to make it useful in commercial tomato or tomato seed production. No variant traits have been observed or are expected for this variety.

Also in accordance with the present invention, there is provided a plant having the physiological and morphological characteristics of tomato variety BX 0154 3756. A description of the physiological and morphological characteristics of tomato variety BX 0154 3756 is presented in Table 3.

TABLE 3

Physiological and Morphological Characteristics of Variety BX 0154 3756

| CHARACTERISTIC | Value for Variety BX 0154 3756* |
|---|---|
| 1. Seedling | |
| Anthocyanin in hypocotyl of 2-15 cm seedling | Present |
| Habit of 3-4 week old seedling | Normal |
| 2. Mature Plant | 200 cm Height |
| Growth | Indeterminate |
| Form | Lax, open |
| Size of canopy (compared to others) | Medium |
| Habit | Sprawling (decumbent) |
| 3. Stem | |
| Branching | Sparse ('Brehm's Solid Red', 'Fireball') |
| Branching at cotyledonary or first leafy node | Absent |
| No. of nodes below the first inflorescence | 4-6 |
| No. of nodes between early (1$^{st}$-2$^{nd}$, 2$^{nd}$-3$^{rd}$) inflorescences | 3-4 |
| No. of nodes between later-developing inflorescences | 3-4 |
| Pubescence on younger stems | Sparsely hairy (scattered long hairs) |
| 4. Leaf (mature leaf beneath the 3$^{rd}$ inflorescence) | |
| Type | Tomato |
| Margins of major leaflets | Shallowly toothed or scalloped |
| Marginal rolling or wiitiness | Slight |
| Onset of leaflet rolling | Late season |
| Surface of major leaflets | Smooth |
| Pubescence | Normal |
| 5. Inflorescence (made observation on 3$^{rd}$ inflorescence) | |
| Type | Simple |
| Number of flowers in inflorescence, average | 10 |
| Leafy or "running" inflorescences | Absent |
| 6. Flower | |
| Calyx | Normal, lobes awl-shaped |
| Calyx-lobes | Approx. equaling corolla |
| Corolla color | Yellow |
| Style pubescence | Sparse |
| Anthers | All fused into tube |
| Fasciation (1$^{st}$ flower of 2$^{nd}$ or 3$^{rd}$ inflorescence) | Absent |

TABLE 3-continued

Physiological and Morphological Characteristics of Variety BX 0154 3756

| CHARACTERISTIC | Value for Variety BX 0154 3756* |
|---|---|
| 7. Fruit ($3^{rd}$ fruit of $2^{nd}$ or $3^{rd}$ cluster) | |
| Abscission layer | Present (jointed) |
| Point of detachment of fruit at harvest | Generally at stem scar, but sometimes at calyx |
| Length of pedicel (from joint to calyx attachment) | 8 mm |
| Length of mature fruit (stem axis) | 23 mm |
| Diameter of fruit at widest point | 20 mm |
| Weight of mature fruit | 7 g |
| No. of locules | 2 |
| Fruit surface | Smooth |
| Fruit base color (mature-green stage) | Light green |
| Fruit pattern (mature green stage) | Green shouldered |
| Shoulder color | Grey green |
| Fruit color - full ripe | Orange |
| Flesh color - full ripe | Orange |
| Flesh color | Uniform |
| Locular gel color of table-ripe fruit | Yellow |
| Ripening | Uniform |
| Epidermis color | Yellow |
| Epidermis | Normal |
| Epidermis texture | Tender |
| Thickness of pericarp | Under 3 mm |
| 8. Disease and Pest Reaction | |
| Viral | |
| Tobacco mosaic, Race 0 | Resistant |
| Tobacco mosaic, Race 1 | Resistant |
| Tobacco mosaic, Race 2 | Resistant |
| Tomato spotted wilt | Susceptible |
| Tomato yellows | Susceptible |
| Bacterial | |
| Bacterial canker (*Corynebacterium michiganense*) | Susceptible |
| Bacterial speck (*Pseudomonas tomato*) | Resistant |
| Bacterial spot (*Xanthomonas vesicatorium*) | Susceptible |
| Bacterial wilt (*Pseudomonas solanacearum*) | Susceptible |
| Fungal | |
| Brown root rot or corky root (*Pyrenochaeta lycopersici*) | Susceptible |
| *Fusarium* wilt, Race 1 | Resistant |
| *Fusarium* wilt, Race 2 | Susceptible |
| *Fusarium* wilt, Race 3 | Susceptible |
| Gray leaf spot (*Stemphylium* spp.) | Susceptible |
| *Verticillium* wilt, Race 1 (*V. albo-atrum*) | Resistant |
| 9. Chemistry and Composition of Full-Ripe Fruits | |
| pH | 4.57 |
| Titratable acidity, as % citric | 5.79 |
| Total solids (dry matter, seeds and skin removed) | 10.01 |
| Soluble solids, as °Brix | 9.53 |
| 10. Phenology | |
| Seeding to 50% flower (1 open flower on 50% of plants) | 45 days |
| Seed to once-over harvest | 78 days |
| Fruiting season | Medium |
| Relative maturity in areas tested | Early |
| 11. Adaptation | |
| Culture | Greenhouse |
| Principal use | Fresh market |
| Machine harvest | Not adapted |
| Regions to which adaptation has been demonstrated | California: Sacramento and Upper San Joaquin Valley |

*These are typical values. Values may vary due to environment. Other values that are substantially equivalent are within the scope of the invention.

Seed of variety BX 0154 3756 has been planted in different years. The plants grown from this seed have shown homozygosity and phenotypic stability to make it useful in commercial tomato production. No variant traits have been observed or are expected for this variety.

C. Breeding Tomato Plants of the Invention

The development of new lines or varieties using one or more starting lines is well known in the art. In accordance with the invention, novel lines may be created by selfing a plant of variety BX 0154 3756 or by crossing a plant of line CHI 15-2113, line CHD 15-2114 or variety BX 0154 3756 with any second plant, followed by multiple generations of breeding according to such well known methods. In selecting such a second plant to cross for the purpose of developing novel lines, it may be desired to choose those plants that either themselves exhibit one or more selected desirable characteristics or that exhibit the desired characteristic(s) when in hybrid combination. Once initial crosses have been made, inbreeding and selection may be undertaking to produce new line and varieties. For development of a uniform line, often five or more generations of selfing and selection are involved.

One aspect of the current invention concerns methods for crossing line CHI 15-2113, line CHD 15-2114 or variety BX 0154 3756 with itself or a second plant and the seeds and plants produced by such methods. Furthermore, the methods of this invention provide for the development of true breeding lines after a plant of line CHI 15-2113 or line CHD 15-2114 has been crossed with a plant of a different line or variety or after a plant of variety BX 0154 3756 has been selfed or crossed with a plant of a different line or variety.

Uniform lines of new varieties may also be developed by way of double-haploids. This technique allows the creation of true breeding lines without the need for multiple generations of selfing and selection. In this manner, true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line CHI 15-2113, line CHD 15-2114 or variety BX 0154 3756 and progeny thereof to achieve a homozygous line.

New true breeding lines may also be developed by combining the methods of classical breeding and the doubled-haploid techniques discussed above. Thus new lines or varieties may be created, for example, by selfing a plant of variety BX 0154 3756 or by crossing a plant of line CHI 15-2113, line CHD 15-2114 or variety BX 0154 3756 with any second plant followed my one or more generations of inbreeding and selection. Doubled haploid techniques may be applied to the plants at any desired generational level to produce true breeding lines.

Backcrossing can also be used to improve an inbred plant or F1 hybrid progeny derived therefrom. Backcrossing transfers one or more heritable traits from one inbred or non-inbred source to an inbred that lacks those traits. The exact backcrossing protocol will depend on the characteristic(s) or trait(s) being altered to determine an appropriate testing protocol. When the term line CHI 15-2113, line CHD 15-2114 or variety BX 0154 3756 is used in the context of the present invention, this also includes plants modified to include at least a first desired heritable trait.

This can be accomplished, for example, by first crossing a superior inbred (recurrent parent) to a donor inbred (non-recurrent parent), which carries the appropriate genetic information (e.g., an allele) at the locus or loci relevant to the trait in question. The progeny of this cross are then mated back to the recurrent parent followed by selection in the resultant progeny (first backcross generation, or BC1) for the desired trait to be transferred from the non-recurrent parent. After five or more backcross generations with selection for the desired trait, the progeny are heterozygous at loci controlling the characteristic being transferred, but are like the superior parent for most or almost all other loci. The last backcross generation would be selfed to give pure breeding progeny for the trait being transferred.

The parental tomato plant which contributes the desired characteristic or characteristics is termed the non-recurrent parent because it can be used one time in the backcross protocol and therefore need not recur. The parental tomato plant to which the locus or loci from the non-recurrent parent are transferred is known as the recurrent parent as it is used for several rounds in the backcrossing protocol.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

In one embodiment, progeny tomato plants of a backcross in which line CHI 15-2113 or line CHD 15-2114 is the recurrent parent comprise (i) the desired trait from the non-recurrent parent and (ii) all of the physiological and morphological characteristics of line CHI 15-2113 or line CHD 15-2114 as determined at the 5% significance level when grown in the same environmental conditions.

Direct selection or screening may be applied where the single locus (e.g. allele) acts in a dominant fashion. For example, when selecting for a dominant allele providing resistance to a bacterial disease, the progeny of the initial cross can be inoculated with bacteria prior to the backcrossing. The inoculation then eliminates those plants which do not have the resistance, and only those plants which have the resistance allele are used in the subsequent backcross. This process is then repeated for all additional backcross generations.

Although backcrossing methods are simplified when the characteristic being transferred is a dominant allele, recessive, co-dominant and quantitative alleles may also be transferred. In this instance, it may be necessary to introduce a test of the progeny to determine if the desired locus has been successfully transferred. In the case where the non-recurrent line was not homozygous, the F1 progeny would not be equivalent. F1 plants having the desired genotype at the locus of interest could be phenotypically selected if the corresponding trait was phenotypically detectable in a heterozygous or hemizygous state. In the case where a recessive allele is to be transferred and the corresponding trait is not phenotypically detectable in the heterozygous of hemizygous state, the resultant progeny can be selfed, or crossed back to the donor to create a segregating population for selection purposes. Non-phenotypic tests may also be employed. Selected progeny from the segregating population can then be crossed to the recurrent parent to make the first backcross generation (BC1).

Molecular markers may also be used to aid in the identification of the plants containing both a desired trait and having recovered a high percentage of the recurrent parent's genetic complement. Selection of tomato plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay that is able to identify the relative presence or absence of a trait of interest in a plant can also be useful for breeding purposes. Procedures for marker assisted selection applicable to the breeding of tomato are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Simple Sequence Repeats (SSR), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

Tomato varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Manipulation of ploidy-level is another technique which can be used to improve an inbred plant. The ploidy level of an organism refers to the number of complete sets of chromosomes typically found in each cell. Natural variation in ploidy level is common among many plants. Since crosses between species that differ in ploidy level may fail or may produce sterile offspring, it may be advantageous to change the ploidy level of one parent so that the ploidy levels are matched before making the cross. For example, in one embodiment of the invention, uniform lines of new tomato varieties may be developed by way of diploid reversions. This technique involves, in the case of a tetraploid, for example, reducing the plant's genome to diploid. Techniques for the reduction of ploidy levels include androgenesis using anther cultures, as reported, for example, in Kopecky et al., 2005. Suitable cells may include microspores, pollen, anther and ovary cultures. A plant produced by such methods for use in the technique is called a diploid reversion. A diploid reversion may then be crossed and/or backcrossed with other diploid tomato plant varieties. After ploidy manipulation and/or breeding is complete, the number of chromosome sets of a suitable diploid progeny plant may be increased back to the original ploidy level (Linstrom, 1940).

Methods for increasing the ploidy level of a diploid plant are also well known in the art. For example, by treating cells of a diploid plant with colchicine, tetraploid plants may be retrieved. Triploids may be formed, for example, by fertilizing a doubled-haploid ovule with haploid pollen. Other techniques for manipulating ploidy levels include somatic hybridization or protoplast fusion. Any of such techniques may be used in accordance with the invention.

Tomatoes are grown for use as rootstocks or scions. Typically, different types of tomatoes are grafted to enhance disease resistance, which is usually conferred by the rootstock, while retaining the horticultural qualities usually conferred by the scion. It is not uncommon for grafting to occur between *Solanum lycopersicum* lines and related *Solanum* species. Methods of grafting and vegetative propagation are well-known in the art.

The lines and varieties of the present invention are particularly well suited for the development of new lines or varieties based on the elite nature of the genetic background of the variety. In selecting a second plant to cross with line CHI 15-2113, line CHD 15-2114 or variety BX 0154 3756 for this purpose, it will typically be preferred to choose those plants that either themselves exhibit one or more selected desirable characteristics or that exhibit the desired characteristic(s) when in hybrid combination. Examples of desirable characteristics may include, but are not limited to herbicide tolerance, pathogen resistance (e.g., insect resistance, nematode resistance, resistance to bacterial, fungal, and viral disease), male fertility, improved harvest characteristics, enhanced nutritional quality, increased antioxidant content, improved processing characteristics, high yield, improved characteristics related to the fruit flavor, texture, size, shape, durability, shelf life, and yield, improved vine habit, increased soluble solids content, uniform ripening, delayed or early ripening, reduced blossom end scar size, seedling vigor, adaptability for soil conditions, and adaptability for climate conditions. Qualities that may be desirable in a processing tomato are not necessarily those that would be desirable in a fresh market tomato; thus, the selection process for desirable traits for each specific end use may be different. For example, certain features, such as solids content, and firm fruit to facilitate mechanical harvesting are more desirable in the development of processing tomatoes; whereas, external features such as intensity and uniformity of fruit color, unblemished fruit, and uniform fruit size are typically more important to the development of a fresh market product that will have greater retailer or consumer appeal. Of course, certain traits, such as disease and pest resistance, high yield, and concentrated fruit set are of interest in any type of tomato line or variety.

D. Performance Characteristics

As described above, variety BX 0154 3756 exhibits desirable agronomic traits, including high sugar content and resistance to tomato mosaic virus. Sugar content of this variety relative to other varieties were the subject of an objective analysis. The results of the analysis are presented below.

TABLE 4

Average Degrees Brix Comparison For Grape Tomatoes

|  | Year 1 | Year 2 |
| --- | --- | --- |
| BX 0154 3756 | 9.74 | 9.43 |
| SANTA | 7.74 | 7.95 |
| CUPID | 7.33 | 7.40 |
| LSD .05 | 0.68 | 0.73 |

Means with a different letter are significantly different based on Waller-Duncan Baysian LSD, K = 100 (P = 0.05).

In both years, the trials were conducted in the same location in Woodland, Calif. Both trials were transplanted during the first week of May and harvested for laboratory evaluation during the first week of August. The average titratable acidity, measured during these trials was about 5.79, which is a moderate level.

As shown above, variety BX 0154 3756 exhibits superior sugar content when compared to competing lines. Tomatoes of variety BX 0154 3756 are also sweeter than those of its parental lines. For example, tomatoes of line CHI 15-2113 were found to have an average degrees Brix of 8.57, with a range of 7.81 to 8.90, and tomatoes of line CHD 15-2114 were found to have an average degrees Brix of 8.98, with a range from 8.16 to 9.23. The higher level of degrees Brix of hybrid variety BX 0154 3756 may result from heterosis, hybrid vigor, or synergistic effects.

One important aspect of the invention thus provides seed of hybrid variety BX 0154 3756 for commercial use.

E. Plants Derived by Genetic Engineering

Many useful traits that can be introduced by backcrossing, as well as directly into a plant, are those that are introduced by genetic transformation techniques. Genetic transformation may therefore be used to insert a selected transgene into the hybrid tomato variety of the invention or may, alternatively, be used for the preparation of lines containing transgenes that can be subsequently transferred to the line of interest by crossing. Methods for the transformation of plants, including tomato, are well known to those of skill in the art. Techniques which may be employed for the genetic transformation of tomato include, but are not limited to, electroporation, microprojectile bombardment, *Agrobacterium*-mediated transformation, pollen-mediated transformation, and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

To effect pollen-mediated transformation, one may apply pollen pretreated with DNA to the female reproductive parts of tomato plants for pollination. A pollen-mediated method for the transformation of tomato is disclosed in U.S. Pat. No. 6,806,399.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target tomato cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant species where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for tomato plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly, partially duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunl, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the tomato lines and varieties of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a tomato plant according to the invention. Non-limiting examples of particular genes and corresponding phenotypes one may choose to introduce into a tomato plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (e.g., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

F. Definitions

In the description and tables herein, a number of terms are used. In order to provide a clear and consistent understanding of the specification and claims, the following definitions are provided:

Alleles: Alternate forms of a single gene.

Backcrossing: A process in which a breeder repeatedly crosses hybrid progeny, for example a first generation hybrid ($F_1$), back to one of the parents of the hybrid progeny. Backcrossing can be used to transfer genetic information (e.g., an allele) from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Locus: A designated location on a chromosome.

Marker: A readily detectable phenotype, preferably inherited in codominant fashion (both alleles at a locus in a diploid heterozygote are readily detectable), with no environmental variance component, i.e., a heritability of 1.

Polyploid: A cell or organism of containing three or more complete sets of chromosomes.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits whose phenotypes are usually continuously distributed.

Regeneration: The development of a plant from tissue culture.

Self-pollination: The transfer of pollen from the anther to the stigma of the same plant.

Single Locus Converted (Conversion) Plant: A plant, often developed through the backcrossing technique, having essentially all of the desired morphological and physiological characteristics of given variety, expect that at one locus it contains the genetic material (e.g., an allele) from a different variety. Genetic transformation may also be used to develop single locus converted plants.

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a tomato plant by transformation.

Triploid: A cell or organism having three sets of chromosomes.

G. Deposit Information

A deposit of tomato line CHI 15-2113, line CHD 15-2114 and hybrid tomato variety BX 0154 3756, disclosed above and recited in the claims, has been made with the American Type Culture Collection (ATCC), 10801 University Blvd., Manassas, Va. 20110-2209. Upon issuance of a patent, all restrictions upon the deposit will be removed, and the deposit is intended to meet all of the requirements of 37 C.F.R. §1.801-1.809. The accession number for those deposited seeds of tomato line CHI 15-2113, deposited on Apr. 24, 2007, is ATCC Accession No. PTA-8378. The accession number for those deposited seeds of tomato line CHD 15-2114, deposited on Jun. 2, 2008, is ATCC Accession No. PTA-9240. The accession number for those deposited seeds of tomato variety BX 0154 3756, deposited on Apr. 24, 2007, is ATCC Accession No. PTA-8379. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 5,378,619
U.S. Pat. No. 6,806,399
WO 99/31248
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997
Gull et al., *J. Amer. Soc. Hort. Sci.* 114:950-954, 1989.
Kader et al. *Hort. Sci.*, 13:577-578, 1978.
Klee et al., *Bio-Technology*, 3(7):637-642, 1985.
Kopecky et al., Crop Science, 45:274-281, 2005.
Kuhlemeier et al., *Plant Cell*, 1:471, 1989.
Linstrom, *Genetics*, 26:387-397, 1940.
Marcotte et al., *Nature*, 335:454, 1988.
Marcotte et al., *Plant Cell*, 1:969, 1989.
Odel et al., *Nature*, 313:810, 1985.
Omirulleh et al., *Plant Mol. Biol.*, 21(3):415-428, 1993.
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 1 8:6531-6535, 1990.

What is claimed is:
1. A tomato plant comprising at least a first set of the chromosomes of tomato line CHD 15-2114, a sample of seed of said line having been deposited under ATCC Accession Number PTA-9240.

2. A seed comprising at least a first set of the chromosomes of tomato line CHD 15-2114, a sample of seed of said line having been deposited under ATCC Accession Number PTA-9240.

3. A plant grown from the seed of claim 2.

4. The plant of claim 1, which is inbred.

5. The plant of claim 1, which is hybrid.

6. A plant part of the plant of claim 1.

7. The plant part of claim 6, further defined as a fruit, a rootstock, a scion, a cell, an ovule and pollen.

8. A tomato plant, or a part thereof, having all the physiological and morphological characteristics of the tomato plant of claim 3.

9. A tomato plant, or a part thereof, having all the physiological and morphological characteristics of the tomato plant of claim 4.

10. A tissue culture of regenerable cells of the plant of claim 1.

11. The tissue culture according to claim 10, comprising cells or protoplasts from a plant part selected from the group consisting of embryos, meristems, cotyledons, pollen, leaves, anthers, roots, root tips, pistil, flower, seed and stalks.

12. A tomato plant regenerated from the tissue culture of claim 10.

13. A method of vegetatively propagating a plant of tomato line CHD 15-2114 comprising the steps of:
(a) collecting tissue capable of being propagated from a plant of tomato line CHD 15-2114, a sample of seed of said line having been deposited under ATCC Accession Number PTA-9240;
(b) cultivating said tissue to obtain proliferated shoots; and
(c) rooting said proliferated shoots to obtain rooted plantlets.

14. The method of claim 13, further comprising growing plants from said rooted plantlets.

15. A method of introducing a desired trait into tomato line comprising:
(a) crossing a plant of line CHD 15-2114, a sample of seed of said line having been deposited under ATCC Accession Number PTA-9240, with a second tomato plant that comprises a desired trait to produce F1 progeny;
(b) selecting an F1 progeny that comprises the desired trait;
(c) crossing the selected F1 progeny with a plant of line CHD 15-2114 to produce backcross progeny;
(d) selecting backcross progeny comprising the desired trait and the physiological and morphological characteristic of tomato line CHD 15-2114; and
(e) repeating steps (c) and (d) three or more times in succession to produce selected fourth or higher backcross progeny that comprises the desired trait.

16. A tomato plant produced by the method of claim 15.

17. A method of producing a plant comprising an added desired trait, the method comprising introducing a transgene conferring the desired trait into a plant of tomato line CHD 15-2114, a sample of seed of said line having been deposited under ATCC Accession Number PTA-9240.

18. A method of determining the genotype of the plant of claim 1 comprising obtaining a sample of nucleic acids from said plant and detecting in said nucleic acids a plurality of polymorphisms, thereby determining the genotype of the plant.

19. The method of claim 18, further comprising the step of storing the results of detecting the plurality of polymorphisms on a computer readable medium.

20. A method for producing a seed of a line derived from tomato line CHD 15-2114 comprising the steps of:
(a) crossing a tomato plant of line CHD 15-2114, a sample of seed of said line having been deposited under ATCC Accession Number PTA-9240, with a second tomato plant; and
(b) allowing seed of a line CHD 15-2114-derived tomato plant to form.

21. The method of claim 20, further comprising the steps of:
(c) crossing a plant grown from said line CHD 15-2114-derived tomato seed with itself or a different tomato plant to yield additional line CHD 15-2114-derived tomato seed;
(d) growing said additional line CHD 15-2114-derived tomato seed of step (c) to yield additional line CHD 15-2114-derived tomato plants; and
(e) repeating the crossing and growing steps of (c) and (d) to generate further line CHD 15-2114-derived tomato plants.

22. The method of claim 20, wherein the second tomato plant is of an inbred tomato line.

23. A method of producing at least a first tomato comprising:
(a) obtaining the plant of claim 1, wherein the plant has been cultivated to maturity; and
(b) collecting at least a first tomato from the plant.

24. A tomato plant produced by the method of claim 17.

25. A seed that produces the plant of claim 16.

26. A seed that produces the plant of claim 24.

* * * * *